United States Patent [19]

Dubroff

[11] Patent Number: 4,575,878
[45] Date of Patent: Mar. 18, 1986

[54] INTRAOCULAR LENSES

[76] Inventor: Seymour Dubroff, 3806 Thornapple, Chevy Chase, Md. 20815

[21] Appl. No.: 494,364

[22] Filed: May 13, 1983

Related U.S. Application Data

[63] Continuation-in-part of Ser. No. 230,279, Jan. 30, 1981, abandoned.

[51] Int. Cl.$^4$ ............................ A61F 1/16; A61F 1/24
[52] U.S. Cl. ........................................................ 623/6
[58] Field of Search .......................................... 3/13, 1

[56]  References Cited

U.S. PATENT DOCUMENTS 4,159,546  7/1979  Shearing ................................... 3/13
4,244,060  1/1981  Hoffer ...................................... 3/13

OTHER PUBLICATIONS

Covered Bridge (Book) An Update on Lens Implantation, by John H. Sheets, M.D., or Bridge over Troubled Waters, 1977, pp. 4–13.
The Simcoe Posterior Chamber Lens (Brochure) by Cilco, Cilco, Inc., 1616 13th Ave., Huntington, West Virginia 25701, Feb. 1980, 5 pages.
The Lindstrom Centrex Style 20 Posterior Chamber Lens, by Surgidev, Surgidev Corp., 1421 State St., Santa Barbara, CA 93101, (Brochure) 4 pages, Jan. 4, 1981.

Primary Examiner—Ronald L. Frinks
Attorney, Agent, or Firm—Epstein & Edell

[57]  ABSTRACT

An intraocular lens for implant in the eye, particularly in the anterior chamber, includes a lens body and at least three flexible, resilient, fixation filaments extending from the periphery of the lens body and having curved intermediate and distal portions to minimize drainage blockage in the angle of intersection of the cornea and the iris while minimizing the risk of passing of a filament through the pupil and tucking a filament in the iris during insertion of the intraocular lens. The use of at least three fixation filaments reduces twisting or turning of the intraocular lens and produces secure centralization of the intraocular lens with increased stability and reduced chance of inadvertent movement of the intraocular lens in the eye.

10 Claims, 7 Drawing Figures

INTRAOCULAR LENSES

This application is a continuation-in-part of application Ser. No. 230,279 filed Jan. 30, 1981, now abandoned.

BACKGROUND OF THE INVENTION

1. Field of the Invention

The present invention pertains to artificial lenses for the eye and, more particularly, to intraocular lenses for surgical implantation in the eye.

2. Discussion of the Prior Art

The implantation of an artificial intraocular lens in an eye after removal of the natural lens due to a blindness-causing condition, such as cataract, has become an accepted practice. Such intraocular lenses are normally positioned in the posterior chamber of the eye, secured to the iris, or positioned in the anterior chamber of the eye. Anterior chamber intraocular lenses are desirable due to their advantages of requiring reduced manipulation for proper placement and of being suitable for use with intracapsular and extracapsular natural lens removal; however, in the past, anterior chamber intraocular lenses have suffered the disadvantages of requiring a precise measurement of the diameter of the anterior chamber or cornea to select the appropriate size implant and of the implanted intraocular lens irritating the cornea by riding thereagainst due to the insufficient flexibility of existing anterior chamber intraocular lenses. If the intraocular lens implanted is too small, movement of the intraocular lens in the anterior chamber can cause corneal irritation; and, if the intraocular lens implanted is too large, the Ugh syndrome, hyphema, and eye tenderness can occur. Accordingly, prior art anterior chamber intraocular lenses have had to be available in all sizes to the surgeon, and the surgeon must accurately determine the diameter of the anterior chamber before insertion of the intraocular lens or subject the patient to the trauma of implanting and removing intraocular lenses on a trial and error basis to find the proper size intraocular lens.

Accordingly, recently, it has become common to utilize posterior chamber intraocular lenses; however, the use of such lenses inherently requires precise and difficult manipulation of the intraocular lens for placement behind the iris; and, additionally, problems arise when the lens capsule is punctured or removed during removal of the natural lens. Thus, implantation of posterior chamber lenses effectively has been limited due to the surgical skill required in removal of the natural lens without puncturing the lens capsule and the surgical skill required to properly manipulate the implant lens for proper positioning in the posterior chamber. Even then, decentered lenses are not rare.

The practice of implanting intraocular lenses after natural lens removal due to cataract or other blindness-causing conditions is ever increasing; and, as more surgeons utilize this practice, rather than utilizing spectacles or contact lenses to provide focusing power after removal of the natural lens, the need for an intraocular lens that can be simply implanted with a minimum of trauma and minimum discomfort to the patient during surgery and thereafter has increased greatly. Thus, there has recently been a return to the use of anterior chamber intraocular lenses, and much effort has been expended to design anterior chamber intraocular lenses of a nature to be easily implanted in the anterior chamber via a single incision. However, such prior art anterior chamber intraocular lenses have had the disadvantages of often not being sufficiently flexible to be comfortably worn by a patient without irritation, not permitting simple implantation, or have created problems with pupillary capture.

In application Ser. No. 230,279, intraocular lenses for positioning in the anterior chamber of the eye are disclosed overcoming the above mentioned disadvantages of the prior art; and, it has been found that the three-point fixation provided by the embodiment of FIG. 10 is most advantageous for positioning in the anterior chamber. Three-point fixation has been proposed for anterior chamber intraocular lenses; however, prior to the invention of application Ser. No. 230,279, such three-point fixation anterior chamber intraocular lenses have utilized relatively rigid positioning members with the concomitant disadvantages mentioned above.

Intraocular lenses for positioning in the posterior chamber having three flexible filaments have been proposed as described in the article by C. William Simcoe in the American Intra-Ocular Implant Society Journal, Volume V, page 357, October, 1979. Intraocular lenses with flexible filaments having shapes similar to that shown in the Simcoe article or J-like shapes extending from lens bodies at various angles have at least one of the disadvantages of blocking the "angle" between the cornea and the iris by positioning too long a length of the filament in the angle when the intraocular lens is in place in the anterior chamber, easy unintentional insertion of the filament through the pupil into the posterior chamber as the intraocular lens is inserted in the anterior chamber and easy unintentional tucking of the filament in the folds of the iris as the intraocular lens is being inserted in the anterior chamber, the latter two disadvantages being greater when it is considered that the pupil and iris are often obscured by blood and aqueous humor during insertion of the intraocular lens.

There has been much effort expended to produce an anterior chamber intraocular lens of universal application due to the surgical complexities of implanting posterior chamber and iris-supported intraocular lenses; however, until the advent of the present invention as described hereinafter and in application Ser. No. 230,279, anterior chamber intraocular lenses have not been satisfactory due to the above described disadvantages thereof.

SUMMARY OF THE INVENTION

Accordingly, it is a primary object of the present invention to overcome the above mentioned disadvantages of the prior art by providing an intraocular lens for positioning in the anterior chamber of the eye having at least three flexible resilient, fixation elements of a shape to minimize drainage blockage in the angle of intersection of the cornea and iris, the opportunity for pupillary capture, insertion of the filament through the pupil and iris tuck.

A further object of the present invention is to prevent pupillary capture and reduce twisting or turning of an intraocular lens in the anterior chamber of the eye by utilizing at least three flexible, resilent filaments.

Another object of the present invention is to support an intraocular lens body with at least three flexible, resilient, fixation filaments each having an intermediate curved portion and a distal curved portion terminating at a free end with the radius of curvature of the intermediate curved portion being greater than the radius of curvature of the distal curved portion.

The present invention has an additional object in the implanting in the anterior chamber of an eye of an intraocular lens having three flexible, resilient, fixation filaments curving from a lens body to free ends to enhance vision after cataract removal with the free ends positioned in the angle of intersection of the cornea and the iris.

Some of the advantages of the present invention over the prior art are that a single size intraocular lens according to the present invention can be utilized for insertion in the anterior chamber of most normal eyes with minimal angle contact, the intraocular lens is easily implanted with reduced risk of insertion of fixation filaments through the pupil and reduced risk of iris tuck, the intraocular lens reduces corneal irritation and is comfortable in plce with decreased post operative tenderness, and the intraocular lens has reduced weight and does not have large, bulk, solid foot plates as do prior art anterior chamber intraocular lenses.

The present invention is generally characterized in an intraocular lens for implant in an eye comprising a lens body, and a plurality of three or more flexible, resilient, fixation filaments extending from the periphery of the lens body to a free end, each of the fixation filaments having a proximal portion secured to the lens body, an intermediate curved portion extending from the proximal portion having a radius of curvature of from 4.5 mm to 6.0 mm and continuing in an arc of from 50° to 65°, and a distal curved portion extending from the intermediate curved portion to the free end having a radius of curvature of from 2.5 mm to 4.0 mm and continuing in an arc of from 75° to 95°.

The present invention is further generally characterized in an intraocular lens for implant in the anterior chamber of an eye comprising a lens body, and three flexible, resilient fixation filaments each including a proximal portion extending from the periphery of the lens body, an intermediate curved portion extending from the proximal portion and having a first radius of curvature to reduce risk of passage of the fixation filament through the pupil and tucking of the fixation filament in the iris during insertion of said intraocular lens in the anterior chamber, and a distal curved portion extending from the intermediate curved portion to a free end to be disposed in the angle of intersection of the cornea and the iris and having a second radius of curvature to minimize the length of the fixation filament disposed in the angle of intersection of the cornea and the iris, the first radius of curvature being greater than the second radius of curvature.

An additional general characterization of the present invention is in a method of enhancing vision after cataract removal from the eye comprising the step of inserting in the anterior chamber of the eye an intraocular lens having a lens body and three flexible, resilient, fixation filaments extending therefrom, the fixation filaments continuously curving to a free end at a distal portion for positioning in the angle of intersection of the cornea and the iris.

Other objects and advantages of the present invention will become apparent from the following description of the preferred embodiment taken in conjunction with the accompanying drawings.

DESCRIPTION OF THE PREFERRED EMBODIMENT

Figure 1:
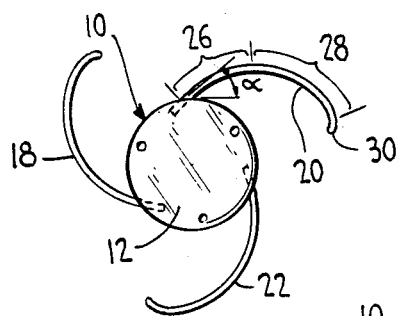
FIG. 1 is a plan view of an intraocular lens according to the present invention.
Figure 2:
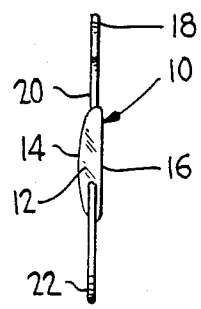
FIG. 2 is a side elevation of the intraocular lens of FIG. 1.

An intraocular lens 10 according to the present invention is shown in FIGS. 1 and 2 and includes a lens body 12 having a generally circular periphery and made of any suitable material for focusing light, preferably a non-degradable and non-toxic plastic. For example, the lens body can be made of polymethylmethacrylate and constructed to a desired prescription and configuration. The lens body 12 has an anterior surface 14, normally having a convex shape, and a posterior surface 16, normally having a flat or planar shape, such that the lens body serves to focus light on the retina in the manner of the natural lens of the eye.

Positioning members 18, 20 and 22 are disposed at equally spaced positions (i.e. 120° apart) on the lens body, and each positioning member is formed of a flexible, resilient, fixation filament. The fixation filaments can have any desirable shape in cross section but are preferably round to provide smooth surfaces. The fixation filaments are formed of a very flexible, resilient material such that the resilience or memory characteristic of the material permits the filaments to be compressed upon placement in the anterior chamber of the eye with the free ends of the filaments springing back to their initial shape to engage the angle of intersection of the cornea and iris. The flexible, resilient material of the filaments can be any non-toxic, non-degradable material such as a plastic, for example, polypropylene. The filaments preferable have a thickness or diameter in the range of from 0.1 mm to 1.25 mm to enhance flexibility thereof such that a single intraocular lens size can be received in anterior chambers of eyes having varying diameters with the curved free ends of the filaments resiliently flexing to be lodged in the angle of intersection of the cornea and the iris.

The lens body 12 preferably has a diameter on the order of magnitude of 6 mm while the distance from the center of the lens body to the free end of each fixation filament is in the range of from 7 mm to 7.5 mm, preferably closer to 7 mm. The shape of the fixation filaments is optimized for flexibility and minimal drainage blockage in the angle while also minimizing the risk of the filaments passing through the pupil or being tucked in folds in the iris during insertion of the intraocular lens in the anterior chamber. The preferred optimum configuration of each fixation filament to produce the above characteristics is as follows: a proximal portion 24 is secured to the lens body 12 and extends at an angle $\alpha$ to the tangent at the point on the periphery of the lens body from which the fixation filament extends of from 26° to 41°, preferably 31° to 36° and specifically 33½°; an intermediate curved portion 26 extends from the proximal portion 24 having a radius of curvature of from 4.0 mm to 6.0 mm, preferably 5.0 mm to 5.5 mm and specifically 5.25 mm, and continues in an arc or length of from 50° to 65°, preferably 55° to 60° and specifically 57.5°; and a distal curved portion 28 extends to a free end from the intermediate curved portion having a radius of curvature of from 2.4 to 4.0 mm, preferably 3.0 mm to 3.5 mm and specifically 3.25 mm, and continues in an arc or length of from 75° to 95°, preferably 82.5° to 87.5° and specifically 85°. To facilitate manipulation of the intraocular lens by a surgeon during insertion, the distal curved portion 28 terminates at its free end at a hook portion 30 turned inwardly toward the lens body 12, the hook portion 30 having a radius of curvature on the order of 0.5 mm, specifically 0.55 mm, and continuing from the end of the distal curved portion 28 in an arc on the order ob 58°.

The fixation filaments can be secured to the lens body in any conventional manner, for example by insertion in a bore in the lens body or by integral formation with the lens body by molding or lathe cutting, it being of primary importance that the filaments remain extremely flexible to minimize trauma and irritation in the eye.

Figure 3:
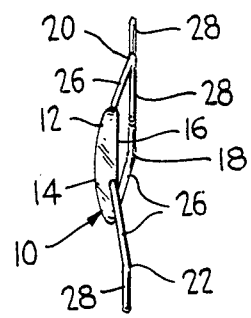
FIG. 3 is a side elevation of the intraocular lens of FIG. 1 with a vaulted configuration.

As illustrated in FIG. 2, the positioning members 18, 20 amd 22 extend in a single plane from the lens body 12; however, if a vaulted configuration is desired to space the lens body from the iris and pupil, the intermediate curved portions 26 of the fixation filaments can extend from the lens body at an angle to the planar posterior surface 16 such that the distal curved portions 28 are spaced from the lens body as shown in FIG. 3.

Figure 4:
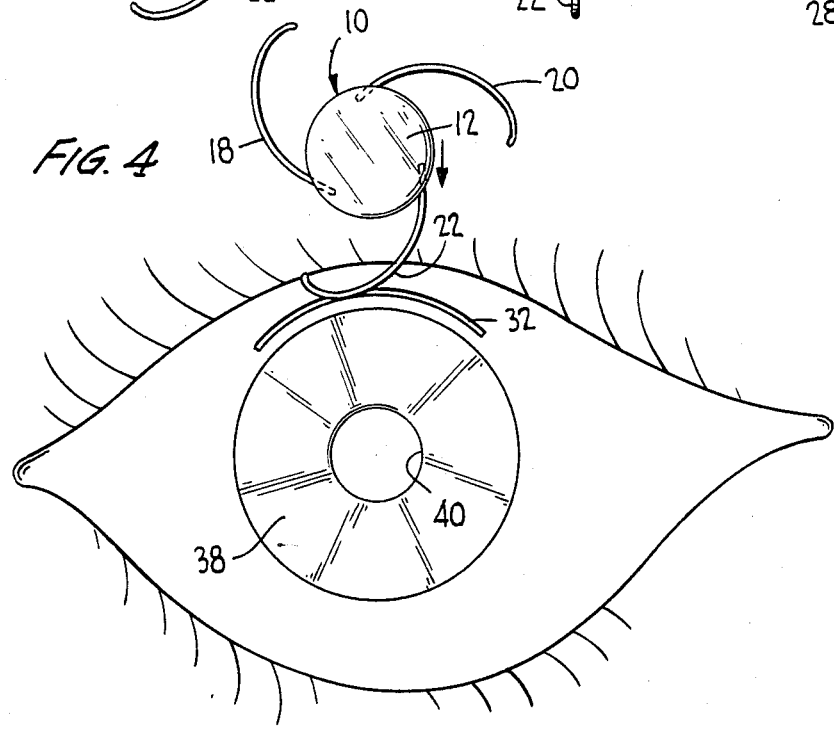
FIGS. 4, 5 and 6 illustrate the insertion of the intraocular lens of the present invention in the anterior chamber.
Figure 5:
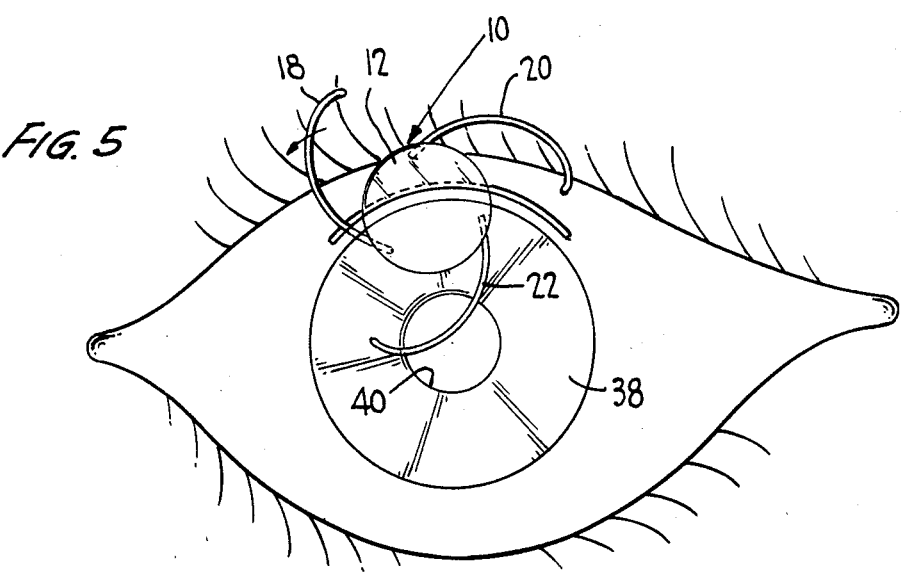
Figure 6:
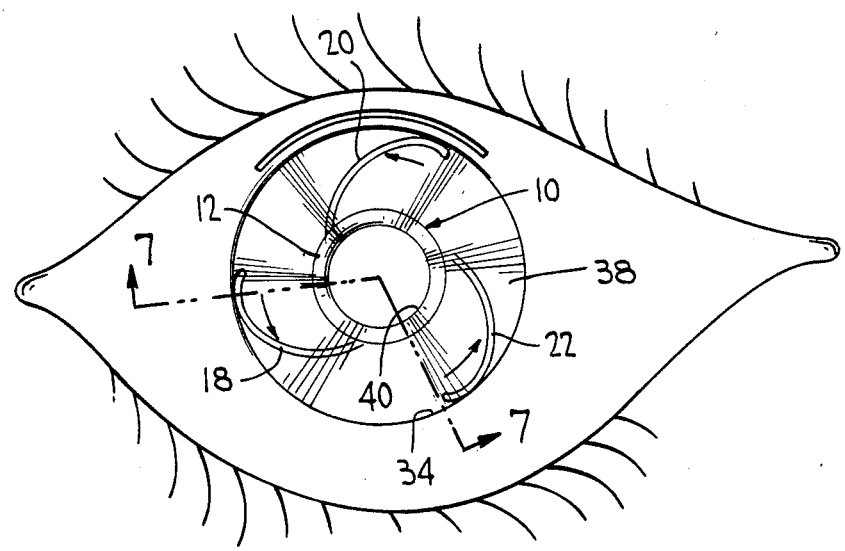
Figure 7:
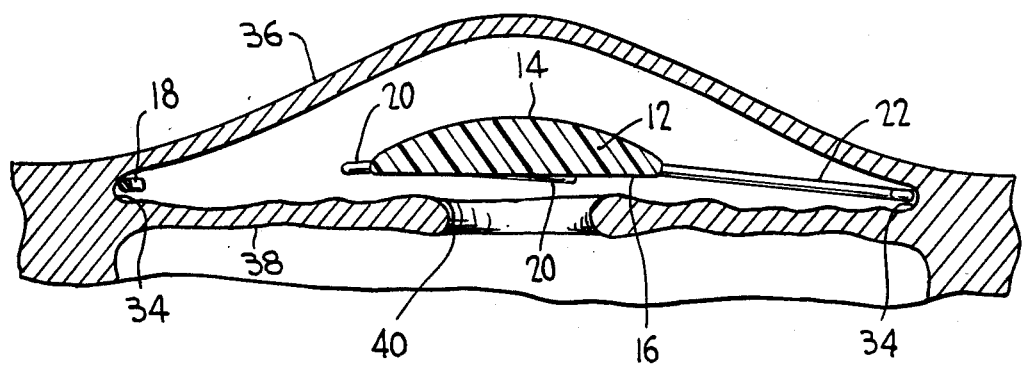
FIG. 7 is a cross sectional view of an intraocular lens according to the present invention in the anterior chamber of the eye taken along line 7—7 of FIG. 6.

To implant the intraocular lens 10 in an eye, positioning member 22 is inserted in an incision 32 in the eye and the intraocular lens is moved radially into the eye, as shown in FIG. 4, in a direct maneuver while holding the lens body with an instrument such as a Clayman-style forceps until approximately half of the lens body is through the incision, as shown in FIG. 5. The positioning member 20 is then grasped by the surgeon with an instrument, such as a McPherson or Dubroff forceps, and rotated or dialed in a direction opposite to the curvature of the fixation filament, counterclockwise looking at FIG. 5, while pushing the intraocular lens completely through the incision, the smooth continuously curving configuration of the fixation filaments facilitating simple, non-traumatic placement in the anterior chamber such that the intraocular lens 10 will be received in the anterior chamber in the position shown in FIG. 6, the scleral lip being lifted over the last inserted fixation filament 20. With the intraocular lens fully inserted, the distal curved portions 28 of the fixation filaments will engage the angle of intersection 34 of the cornea 36 and the iris 38 with the lens body 12 positioned in front of the pupil 40, as shown in FIG. 12.

The flexible, resilient characteristic of the fixation filaments permits compression of the filaments during implant of the intraocular lens and permits a single intraocular lens size to be implanted in most normal eyes regardless of variations in the diameter of the angle of intersection 34 of the cornea and iris since the resilience or spring-like memory of the filaments assures lodging in the angle of intersection. Accordingly, measurement of the diameter of the angle of intersection is obviated, and the trauma associated with the insertion and removal of an intraocular lens of incorrect size is avoided as well as the problems associated with prior art anterior chamber intraocular lenses when the intraocular lens is either too large or too small. By using at least three fixation filaments, the stability of fixation in the anterior chamber is greatly increased since twisting or turning about any axis across the lens body is effectively prohibited and pupillary capture is prevented.

The specific configuration of the fixation filaments of the intraocular lens of the present invention overcomes the problems that would be associated with prior known intraocular lens filament configurations if such filament configurations were utilized with an anterior chamber intraocular lens. That is, the radius of curvature and the arc of the distal curved portion minimizes the length of the fixation filament disposed in the angle 34 whereas with a filament of the configuration shown in the above mentioned Simcoe article a substantially greater length of filament would be disposed in the angle. Since the angle drains fluid, the length of filament disposed therein should be minimized to reduce drainage blockage; however, if a J-like filament is used, while drainage blockage in the angle is reduced, flexibility is decreased and the risk of insertion of a filament through the pupil and iris tuck is increased. With the filament configuration of the present invention, flexibility is maintained, the risk of insertion through the pupil and iris tuck are minimized due to the curved intermediate and distal portions, and drainage blockage is minimized. The radius of curvature of the intermediate portion is greater than the radius of curvature of the distal portion to provide these features and, preferably, the radius of curvature of the intermediate portion is 1.4 to 1.8 times greater than the radius of curvature of the distal portion. Additionally, the configuration of the fixation filaments of the present invention creates sufficient flexibility of support to prevent pupillary fluid block without requiring a vault thereby reducing the risk of corneal contact while simultaneously limiting twisting or turning of the lens, establishing secure centration of the lens in the eye and providing increased stability with reduced chance of inadvertent movement in the eye.

Inasmuch as the present invention is subject to many variations, modifications and changes in detail, it is intended that all subject matter discussed above or shown in the accompanying drawings be interpreted as illustrative and not in a limiting sense.

I claim:

1. An intraocular lens for implant in an eye comprising
    a lens body; and
    a plurality of three or more flexible, resilient, fixation filaments extending from the periphery of said lens body to a free end, each of said fixation filaments having a proximal portion secured to said lens body, an intermediate curved portion extending from said proximal portion having a radius of curvature of from 4.5 mm to 6.0 mm and continuing in an arc of from 50° to 65°, and a distal curved portion extending from said intermediate curved portion to said free end having a radius of curvature of from 2.5 mm to 4.0 mm and continuing in an arc of from 75° to 95°.

2. An intraocular lens as recited in claim 1 wherein said distal portion of each of said fixation filaments includes a hook portion turned inwardly toward said lens body.

3. An intraocular lens as recited in claim 2 wherein said proximal portion of each of said fixation filaments extends from the periphery of said lens body at an angle to the tangent at the point on the periphery from which said fixation element extends of from 26° to 41°.

4. An intraocular lens as recited in claim 3 wherein the radius of curvature of said distal curved portion of each of said fixation filaments is from 3.0 mm to 3.5 mm.

5. An intraocular lens as recited in claim 4 wherein the radius of curvature of said intermediate curved portion of each of said fixation filaments is from 5.0 mm to 5.5 mm.

6. An intraocular lens as recited in claim 5 wherein the arc of said intermediate curved portion is from 55° to 60° and the arc of said distal curved portion is from 82.5° to 87.5°.

7. An intraocular lens as recited in claim 6 wherein said hook portion has a radius of curvature on the order of 0.5 mm and an arc on the order of 58°.

8. An intraocular lens as recited in claim 7 wherein said proximal portion extends from the periphery of said lens body at an angle of from 31° to 36°.

9. An intraocular lens as recited in claim 1 wherein said proximal portion of each of said fixation filaments extends from the periphery of said lens body at an angle to the tangent at the point on the periphery from which said fixation element extends of from 26° to 41°.

10. An intraocular lens as recited in claim 9 wherein for each of said fixation filaments the radius of curvature of said distal curved portion is from 3.0 mm to 3.5 mm, the arc of said distal curved portion is from 82.5° to 87.5°, the radius of curvature of said intermediate curved portion is from 5.0 to 5.5 mm and the arc of said intermediate curved portion is from 55° to 60°.

* * * * *